United States Patent [19]

Wilkinson

[11] Patent Number: 4,561,294

[45] Date of Patent: Dec. 31, 1985

[54] METHOD AND APPARATUS TO CONTROL SOIL MOISTURE MATRIC POTENTIAL

[75] Inventor: Henry T. Wilkinson, Champaign, Ill.

[73] Assignee: The United States of America as represented by the Secretary of Agriculture, Washington, D.C.

[21] Appl. No.: 650,737

[22] Filed: Sep. 14, 1984

[51] Int. Cl.[4] .................. G01N 19/10; G01N 33/24
[52] U.S. Cl. ........................................... 73/73
[58] Field of Search ................................. 73/73, 38

[56] References Cited

U.S. PATENT DOCUMENTS 3,871,211 3/1975 Tal ............................................ 73/73
4,137,931 2/1979 Hasenbeck ........................... 73/73 X

OTHER PUBLICATIONS

*Soil and Water,* D. Hillel, Academic Press, New York, pp. 72–77, (1971).

*Primary Examiner*—Stewart J. Levy
*Assistant Examiner*—Joseph W. Roskos
*Attorney, Agent, or Firm*—M. Howard Silverstein; David G. McConnell; Margaret A. Connor

[57] ABSTRACT

An apparatus and method of use for controlling the matric potential of a porous sample in a liquid are described. The apparatus includes a cylindrical porous cup for holding the sample, the cup having an air entry value greater than the matric potential to be imparted to the sample, an outer vesicle adapted to define a chamber between the cup and vesicle for holding the liquid, and means for adjusting the pressure of the liquid in the chamber.

11 Claims, 2 Drawing Figures

METHOD AND APPARATUS TO CONTROL SOIL MOISTURE MATRIC POTENTIAL

BACKGROUND OF THE INVENTION

This invention relates to and has among its objects the provision of a novel method and apparatus for controlling the matric potential of a liquid in a porous medium (matrix) particularly water in soil.

A liquid such as water can have different energy states. Water which is pure and free is arbitrarily defined as being at zero energy potential. Positive pressure on water increases the potential energy, and negative pressure or suction decreases the potential energy. In addition to pressure, gravitation and solutes can increase and decrease, respectively, the potential energy of water. The influence of gravitation is apparent only in saturated soils and a noticeable effect from solutes occurs only when their concentration is very high. In unsaturated soil, the dominant parameter of the water's potential energy is matric force of matrix suction which results from capillary and adsorptive forces. The capillary forces are dictated by the three dimensional geometry of the porous matrix and the adsorptive forces are controlled by the surfaces of the matrix material. Water will move in a matrix from a point of greater potential energy to a point of lower potential energy. The movement of water will cease when all water is of the same potential energy throughout the matrix, that is, when it is at equilibrium.

The control of the energy of a liquid in a matrix, such as water in soil, which results from matric forces, is important in the study of biological phenomena such as the amount of water needed for the movement of biological propagules, the effects of soil moisture on the availability of oxygen, the transfer of nutrients in soil water, and the transfer of heat sufficient for enzymatic reactions to take place in plant roots. For example, a controlled soil moisture matric potential is important in the study of the colonization of roots by bacteria.

Devices currently available for providing a constant matric potential to a rigid porous sample comprise a horizontal porous ceramic tension plate having an air entry value greater than the sample, and adapted for supporting the sample on a head of water, below. The pressure applied to the head of water is negative with respect to the atmospheric pressure, or the gas pressure otherwise applied to the sample from above. For the control of the matric potential of water in the sample, water potential must be equilibrated on both sides of the ceramic plate. The time required for equilibration is a function of the porosity of the plate, the porosity of the sample (e.g., soil), the initial difference between the matric potential on the opposite sides of the plate, and the maximum distance of any particle of the sample to the ceramic plate. Of course in the case of the planar tension plate device, the maximum distance of any particle to the plate is equal to the sample thickness.

The primary deficiency of this device relates to the fact that the equilibration time is an exponential function of the sample thickness. Therefore, as a practical matter, the matric potential can only be controlled for samples up to about 3 cm thick, because the time required for equilibration beyond that thickness becomes prohibitive. For example, in the laboratory study of biological phenomena in soil water, an equilibration period of no greater than 48 hours is desirable. An apparatus capable of maintaining a constant matric potential in thicker samples would be of paramount importance because a large percentage of all root associated microbial activity occurs in unsaturated soil at depths greater than 3 cm.

SUMMARY OF THE INVENTION

The invention described herein provides means for obviating the above described problems. The device of the invention utilizes an omnidirectional approach for controlling the matric potential of a liquid in a rigid porous sample whereby the sample is placed in a cylindrical porous cup having an air entry value greater than the matric potential to be imparted to the sample. The cup is secured within a chamber in which the liquid pressure exerted on the cup and the contained sample can be adjusted to a predetermined value. By virtue of this arrangement, the maximum distance of any particle of the sample from the sample support is determined by the porous cup inner radius and not the thickness of the sample as in the prior art devices.

In accordance with this discovery, it is an object of the invention to provide a device for the control of the matric potential of a liquid in a porous sample wherein the equilibration time is independent of sample depth.

It is also an object of the invention to provide a device for controlling the matric potential in samples greater than 3 cm without prohibitively long equilibration times.

It is a particular object of the invention to apply the aforementioned device to soil samples for the study of biological phenomena.

Other objects and advantages of the invention will become readily apparent from the ensuing description.

DETAILED DESCRIPTION OF THE INVENTION

Figures 1, 2:
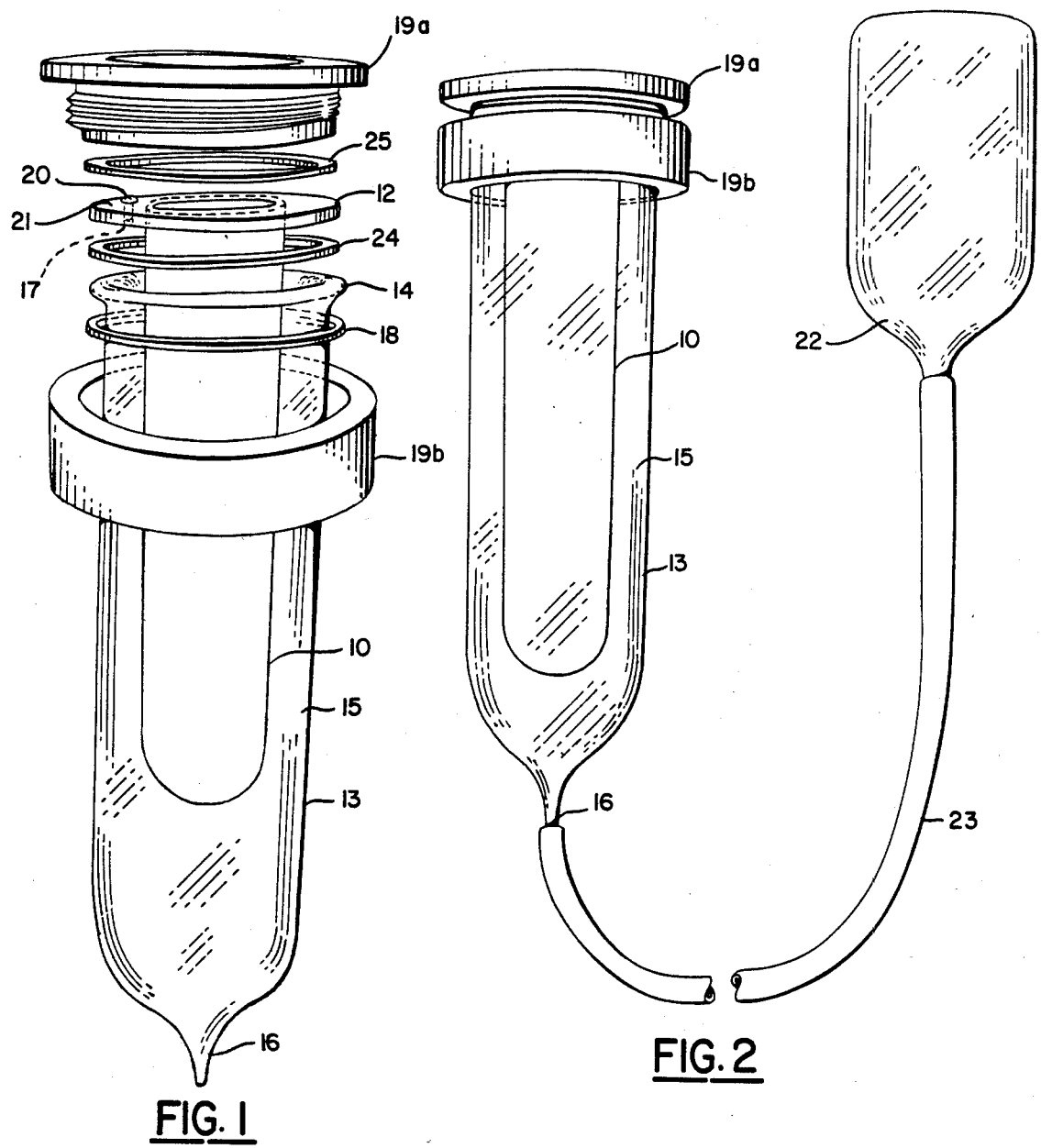
FIG. 1 is an exploded elevational view of the device for controlling the matric potential of a liquid in a porous sample.
FIG. 2 is an elevational view of the assembled device shown in FIG. 1 with reservoir attached.

In the ensuing disclosure, reference to use of the invention to control the matric potential of water in soil is illustrative. It is to be understood that the invention may be used to control the matric potential of a liquid in any textured medium, for example, glass or synthetic beads.

Referring to FIGS. 1 and 2, the invention includes porous cylindrical cup 10 which is open at one end to permit introduction of the porous sample, e.g. soil, into the cup. Attached at or near the upper open end of cup 10 and extending outward therefrom is a flange equipped with a closeable vent 17. A vesicle 13 having lip 14 adapted to sealingly engaged with flange 12 surrounds cup 10 to define chamber 15 therebetween for holding a liquid; with the outer surface of cup 10 defining the inner wall of the chamber, the inner surface of vesicle 13 defining the outer side and bottom walls of the chamber and the lower surface of flange 12 defining the upper wall of the chamber. The bottom of vesicle 13 tapers to inlet 16 which communicates with liquid reservoir 22 by means of tubing 23 for adjusting the pressure of the liquid in the chamber. The top of reservoir 22 is open to the ambient. Resilient gasket 24 inserted between flange 12 and lip 14 aids in sealing chamber 15 against direct entry of air during use. The assembly is held together by means of a two-part clamp comprising mating, threaded fittings 19a and 19b, which when screwed together compress gasket 24 between the upper surface of lip 14 and the lower surface of flange 12. Resilient gaskets 18 and 25 are also provided to protect flange 12 and lip 14 against fracture in the event that fittings 19a and 19b are excessively tightened. Both parts of the clamp are annular, as of course are the gaskets 18, 24 and 25. The inner diameters of clamp member 19b and gasket 18 must be sufficient to accomodate the outside diameter of vesicle 13. The inner diameters of member 19a and gasket 25 should be sufficient to expose the entirety of the opening in cup 10 and to provide access to vent screw 20. Reservoir 22, which is open on top to the ambient, communicates with inlet 16 by means of tube 23.

Cup 10 is a fabricated rigid, porous material which is permeable to the liquid whose matric potential is to be controlled. The cup can be made of a material having a predetermined air entry value correlated to the amount of suction which will cause air to displace the liquid in the pores. Air entry values are dependent on the construction procedure used to control the porosity of the material and are directly related to the radius of the pores. Materials with very fine pores will permit air to enter only at high pressures whereas materials with coarse pores will permit air to enter at lower pressures. As a practical matter, air entry value of the porous cup should be greater than the matric pressure to be applied to the sample. Under normal atmospheric conditions, the maximum matric potential which can be applied to the system is about 1 bar. Therefore, an air entry value exceeding 1 bar would be sufficient for most situations. To establish matric potentials greater than the ambient atmospheric pressure the entire device must be placed in a pressurized container and the air entry value of cup 10 must correspondingly be selected to exceed the elevated pressure. An exemplary porous material for the control of soil moisture matric potential is ceramic. The flange 12 may be fabricated from some other rigid material such as glass, plastic and the like that can be annealed to the cup.

The radius of cup 10 which in turn determines the maximum distance of any particle of the sample from the inner wall of cup 10 is critical so that equilibration time is not excessively long. This distance is determined experimentally by measuring equilibration time versus the maximum distance of the sample to the rigid matric of the cup. This can be conveniently done by placing various thicknesses of the porous sample on a planar tension plate described previously and measuring equilibration time at each thickness. The thickness giving the desired equilibration time determines the inner radius of porous cup 10 when cup 10 is made of the same rigid porous material as the tension plate. In a laboratory setting to control the matric potential of water in soil, it is desirable that each equilibration period be no greater than about 48 hours. It has been found experimentally that for most agricultural soils using a porous cup made of a rigid porous matrix having an air entry pressure of 1.0 bar, a radius of not greater than 3 cm gives an equilibration time of not greater than about 48 hours. It is preferred that the bottom of cup 10 be hemispherical with the inner radius of the hemisphere being the same as the inner radius of the cylindrical portion of cup 10 to provide uniform equilibration.

Cup 10 can be any depth (vertical height), however as the depth increases, the difference in the matric potential in the porous medium at the top and the bottom of the cup increases. Generally, the difference in matric potential of liquid at the top or bottom of the sample should deviate from the value at the midpoint by no more than about 20%. In the control of soil moisture matric potential where the diameter of the cup is about 3 cm, a suitable maximum depth is about 20 cm. For laboratory use, a height range of about 3 to 20 cm is practical.

Vesicle 13 is preferably fabricated of transparent rigid material so that the presence of any bubble trapped in the liquid in chamber 15 can be visually detected. Materials of choice are glass and rigid plastic. The dimensions of vesicle 13 are not critical so long as it is sufficient size to surround cup 10 and form a chamber therebetween for holding liquid.

Gaskets 18, 24, and 25 and O-ring 21 are made of a resilient material, such as rubber, which provides an air-tight seal. Clamp fittings 19a and 19b can be fabricated of any strong, rigid material such as brass, stainless steel or plastic. Alternate material for sealing chamber 15 are well-known and are encompassed by the invention.

Reservoir 22 and tubing are preferably constructed of transparent, noncollapsing material to allow detection of any gas bubbles entrapped in the liquid. The tubing should be sufficiently flexible to permit raising and lowering the reservoir.

In the operation of the invention, chamber 15 is filled with the liquid whose matric potential is to be controlled. The liquid can be supplied from reservoir 22 by gravitational flow. Entrapped gas is allowed to escape from vent 17, and then screw 20 is tightened over O-ring 21 to seal chamber 15.

Cup 10 is thereafter filled with the porous sample. Upon adding the sample to the cup, a potential energy gradient results between the water in chamber 15, the water in the porous cup, and the water in the sample because there is greater potential energy in the water in chamber 15 than in the sample. Because water will move from a location of higher potential energy to a location of lower potential energy, water will move from chamber 15, through the porous cup and into the sample. This movement will continue until the potential energy of the water in the porous sample equals that in chamber 15. By initially setting the water level in reservoir 22 equal in height to the top of the porous cup and adding the sample into the cup, the sample will become saturated i.e., zero energy potential. This is the greatest potential energy obtainable in this apparatus and can serve as an arbitrary starting potential for all subsequent adjustments in the potential energy of the system. As the potential energy in the porous sample is reduced by lowering reservoir 22, pores in the sample will empty of water and fill with air. If reservoir 22 is lowered so far as to exceed the air entry value of the cup matrix, the liquid in the pores of the cup will be displaced with air. At that point, the continuous gradient of potential energy of the water in the system is lost and matric potential can no longer be controlled.

In the control of soil moisture matric potential, the degree of negative pressure (suction) applied to the soil is correlated to the distance the reservoir is lowered by the relationship $\psi = \Delta H / K$, where $\psi$ is the matric potential, $\Delta H$ is the distance that the water level in the reservoir is lowered from the level of zero energy potential, and K is a constant representing the height of a column of liquid supported by the atmosphere. For water, K is equal to 1076 cm/bar. If for example, a matric potential of water equal to 0.1 bar is desired at a particular reference point in the sample column, then the water level is lowered to 107.6 cm below that point. As practical matter, an upper limit of 0.8 bar and a lower limit of 0 bar matric potential can be critically controlled, although matric potentials as high as 1.0 bar can be carried out with the invention. The greater the negative pressure desired, the more time is required for equilibration.

The following example is given to illustrate the method and device of the invention to control the matric potential of water in soil. It is not intended to limit the scope of the invention which is defined by the claims.

EXAMPLE

The porous cup obtained commercially from Soil Equipment Corporation, Santa Barbara, CA as Part No. 65X18-BIM3, consisted of a ceramic, round bottomed cylindrical tube having an air entry value of 1.0 bar (1076 cm of water) and the following dimensions: height 19.05 cm; outside diameter, 2.00 cm; inside diameter, 2.97 cm; and wall thickness 0.51 cm. An annular plexiglass flange having an outer radius of 7 cm and an inner radius of 3 cm and a thickness of 2 mm was sealed to the top surface of cup 10 as shown in FIG. 1, using epoxy adhesive. A threaded vent was tapped in the flange at a distance of about 7 mm from the outer edge and was sealed with a round-head machine screw (8-32) and rubber O-ring.

The outer vesicle was a cylindrical glass tube tapered at the bottom and having a 5.5 mm lip at the top. The dimensions of the vesicle were as follows: height 20.5 cm; outside diameter, 5.8 cm; wall thickness, 2 mm. Inlet 16 had an inside diameter of 4 mm. The resilient gaskets were made of rubber; gaskets 24 and 25 had an outer diameter of 7 cm and an inner diameter of 4.8 cm and a thickness of 1.5 mm. Gasket 18 was identical except that the inner diameter was 6 cm. The flange, the lip of the outer vesicle and gaskets were clamped together to form an airtight seal by means of mated brass fittings having 12 threads/inch. The water reservoir had a capacity of 1.0 liters. Thick walled tygon tubing was used to connect the reservoir with the chamber inlet.

The porous medium was silt loam from the Moses Lake Area of Washington state.

The invention was carried out as follows. Cup 10 was presoaked in degassed water to displace air from the pores. Vesicle 13 was filled with degassed water from reservoir 22. Prewetted porous cup 10 was then inserted into filled vesicle 13 and the device was sealed as previously described. To insure that chamber 15 was void of all residual air, reservoir 22 was raised so that the level of the water was at a height slightly greater than the top of porous cup 10 and screw 20 was momentarily loosened. Next, soil which had been air-dried to insure uniform packing was introduced into cup 10 until the level was slightly above the top. Then the level of water in reservoir 22 was set equal to the height of the top of the soil in cup 10 and the soil was allowed to attain a state of saturation. Three predetermined matric potentials ($-65$ mbar, $-106$ mbar, and $-268$ mbar) were applied to the vertical midpoint of the soil column by adjusting the reservoir height according to the aforementioned relationship between water level differential and applied suction. The water in the device was allowed to equilibrate. This equilibration period was determined by periodically measuring water content in small aliquots of the soil removed from cup 10. Water contents at the midpoint and at 1 cm intervals above and below the midpoint were determined gravimetrically by oven drying a sample to constant weight and computing the mass ratio (weight loss in drying) to soil (weight of dried sample). When the water content did not change with successive samples, equilibration had been achieved. The matric potential at each interval was calculated. The results are reported in Table I, below.

The variation in water content (w) from the top to the bottom of the column is a function of texture and the matric potential. As shown by the data in Table I, the gradient in w over the height of the soil column (16 cm) is not statistically significant. However, for a given soil type, the gradient in w between the top and the bottom of the column will tend to increase as the water content decreases. As is the case for all soil water content studies, each soil type or other porous medium must be individually characterized to determine the relationship between $\psi$ and w in order to insure valid experimental results. For example, in a silt loam soil, equilibration was apparently achieved after 24 hours when $\psi$ was changed from 0.0 mbar to $-106$ mbar, and 48 hours when $\psi$ was changed from 0.0 mbar to $-268$ mbar.

TABLE I

| Height above Midpoint (cm) | $\psi_v{}^x = -65$ mbar | | $\psi_v = -106$ mbar | | $\psi_v = -268$ mbar | |
|---|---|---|---|---|---|---|
| | $\phi_w$ g H$_2$O/g soil | $\psi$ −mbar | $\phi_w$ g H$_2$O/g soil | $\psi$ −mbar | $\phi_w$ g H$_2$O/g soil | $\psi$ −mbar |
| +8 | 0.36 | 72.2 | 0.28 | 113.4 | 0.19 | 275.4 |
| +7 | 0.37 | 71.5 | 0.24 | 112.5 | 0.18 | 274.5 |
| +6 | 0.38 | 70.6 | 0.27 | 111.6 | 0.20 | 273.6 |
| +5 | 0.35 | 69.6 | 0.37 | 110.6 | 0.20 | 272.6 |
| +4 | 0.35 | 68.7 | 0.39 | 109.7 | 0.21 | 271.7 |
| +3 | 0.36 | 67.8 | 0.35 | 108.8 | 0.21 | 270.8 |
| +2 | 0.37 | 66.9 | 0.32 | 107.9 | 0.20 | 269.9 |
| +1 | 0.38 | 65.9 | 0.34 | 106.9 | 0.22 | 268.9 |
| 0 | 0.39 | 65.0 | 0.36 | 106.0 | 0.22 | 268.0 |
| −1 | 0.39 | 64.1 | 0.36 | 105.1 | 0.21 | 267.1 |
| −2 | 0.39 | 63.1 | 0.35 | 104.1 | 0.21 | 266.1 |
| −3 | 0.40 | 62.2 | 0.34 | 103.2 | 0.21 | 265.2 |
| −4 | 0.40 | 61.3 | 0.34 | 102.3 | 0.21 | 264.3 |
| −5 | 0.40 | 60.4 | 0.35 | 101.4 | 0.22 | 263.4 |
| −6 | 0.41 | 59.4 | 0.34 | 100.4 | 0.21 | 262.4 |
| −7 | 0.40 | 58.5 | 0.36 | 99.5 | 0.23 | 261.5 |

TABLE I-continued

| Height above Midpoint (cm) | $\psi_\gamma{}^x = -65$ mbar $\phi_w$ g H₂O/g soil | $\psi$ −mbar | $\psi_\gamma = -106$ mbar $\phi_w$ g H₂O/g soil | $\psi$ −mbar | $\psi_\gamma = -268$ mbar $\phi_w$ g H₂O/g soil | $\psi$ −mbar |
|---|---|---|---|---|---|---|
| −8 | 0.42 | 57.6 | 0.37 | 98.6 | 0.22 | 260.6 |

$^x\psi_\gamma$ is the matric potential (mbars) at the midpoint of the soil column.

Having thus defined my invention, I claim:

1. A device for controlling the matric potential of a liquid in a porous sample, comprising:
   (a) a porous cup having an opening at the top and a closed bottom, the height of the cup being greater than the radius, wherein said cup is penetrable by said liquid and has an air entry value exceeding a predetermined matric potential to be imparted to said sample;
   (b) an outer vesicle having a rim at the top defining an opening and having an inlet at the bottom, wherein said vesicle is adapted to securely receive said cup so as to define a chamber between said cup and said vesicle, said chamber being isolated from the opening of the cup; and
   (c) means communicating with said inlet for filling said chamber with liquid and for adjusting the pressure of the liquid in said chamber.

2. The device of claim 1 wherein the opening of the porous cup is isolated from the chamber by means of a flange extending outwardly from said opening and adapted to sealingly engaged the rim of said vesicle.

3. The device of claim 2 further comprising a closeable vent in said flange communicating with said chamber.

4. The device of claim 1 wherein said means for adjusting the pressure of the liquid in said chamber comprised a vertically adjustable reservoir and a flexible tube connecting said reservoir with said inlet.

5. The device of claim 1 wherein the porous cup is essentially cylindrical with a hemispherical bottom substantially the same inner radius as the cylindrical portion of the cup.

6. The device of claim 1 wherein the porous sample is soil, the liquid is water, and the cup is made of ceramic.

7. The device of claim 1 wherein said vesicle is transparent.

8. A method for controlling the matric potential of a liquid in a porous sample, comprising the following steps:
   (a) providing a device comprising:
      (1) a porous cup having an opening at the top and a closed bottom, the height of the cup being greater than the radius, wherein said cup is penetrable by said liquid and has an air entry value exceeding a predetermined matric potential to be imparted to said sample;
      (2) an outer vesicle having a rim at the top defining an opening and having an inlet at the bottom, wherein said vesicle is adapted to securely receive said cup so as to define a chamber between said cup and said vesicle, said chamber being isolated from the opening of the cup; and
      (3) means communicating with said inlet for filling said chamber with liquid and for adjusting the pressure of the liquid in said chamber;
   (b) filling the chamber with liquid;
   (c) sealing the chamber;
   (d) filling the cup with the sample;
   (e) allowing the liquid to move from the chamber through the cup until the sample is saturated;
   (f) decreasing the pressure of the liquid in the chamber to correspond to said predetermined matric potential; and
   (g) allowing the liquid in the chamber to equilibrate with the liquid in the sample.

9. The method of claim 8 wherein the sample is soil, the liquid is water, and the porous cup is ceramic.

10. A method for controlling the matric potential of a degassed liquid in a porous sample, comprising the following steps:
    (a) providing a device comprising:
       (1) a porous cup having an opening at the top and a closed bottom, the height of the cup being greater than the radius, wherein said cup is penetrable by said liquid and has an air entry value exceeding a predetermined matric potential to be imparted to said sample;
       (2) an outer vesicle having a rim at the top defining an opening and having an inlet at the bottom, wherein said vesicle is adapted to securely receive said cup so as to define a chamber between said cup and said vesicle, said chamber being isolated from the opening of the cup;
       (3) a vertically adjustable reservoir and a flexible tube connecting said reservoir with said inlet for adjusting the pressure of the liquid in said chamber;
    (b) degassing the porous cup by soaking it in said degassed liquid;
    (c) filling said vesicle with degassed liquid;
    (d) inserting said cup into said liquid-filled gas;
    (e) venting said chamber to remove entrapped gas;
    (f) sealing the chamber;
    (g) filling the cup with the sample;
    (h) adjusting the reservoir to a height so the surface of the liquid in the reservoir is at a level at least as high as the uppermost surface of the sample in said cup and allowing the liquid to migrate into the cup until the sample is saturated;
    (i) lowering the reservoir so that the surface of the liquid is below the uppermost surface of the sample to decrease the pressure of the liquid in the chamber to correspond to said predetermined matric potential; and
    (j) allowing the liquid in the sample to equilibrate with the liquid in the chamber.

11. The method of claim 10 wherein the sample is soil, the liquid is water, and the porous cup is ceramic.

* * * * *